United States Patent [19]

Thompson et al.

[11] Patent Number: 4,824,529
[45] Date of Patent: Apr. 25, 1989

[54] LIPID MEMBRANE-BASED DEVICE

[75] Inventors: Michael Thompson; Ulrich J. Krull, both of Mississauga; Krishna M. Kallury, Scarborough, all of Canada

[73] Assignee: Allied-Signal Inc.

[21] Appl. No.: 125,849

[22] Filed: Nov. 27, 1987

[51] Int. Cl.$^4$ .................... G01N 27/30; G01N 27/40
[52] U.S. Cl. .................... 204/1 T; 204/403; 204/415; 324/425; 324/439; 435/4; 435/7; 435/11; 435/291; 435/817
[58] Field of Search .................... 204/403, 415, 1 T; 435/4, 7, 11, 291, 817; 324/425, 439; 73/23

[56] References Cited

U.S. PATENT DOCUMENTS 4,637,861 1/1987 Krull et al. .................... 204/1 T
4,661,235 4/1987 Krull et al. .................... 204/414

OTHER PUBLICATIONS

Krull et al., Abstract 11-2, 67th Annual CIC Conference (Jun. 1984), "Chemoreceptive Membranes From Langmuir-Blodgett Thin-Film Technology".

Heckmann et al., *Thin Solid Films*, 99: 265 (1983), "Hyperfiltration Through Cross-Linked Monolayers".
Thompson et al., *Talanta*, 30: 919 )1983), "The Bilayer Lipid Membrane as a Basis for a Selective Sensor for Ammonia".

*Primary Examiner*—G. L. Kaplan
*Attorney, Agent, or Firm*—Timothy R. Kroboth; Gerhard H. Fuchs

[57] ABSTRACT

A protected, lipid membrane-based device useful as a chemoreceptive transducer is provided. The device includes a porous, membrane-protective layer attached to an underlying, lipid membrane. Also provided is a process for using the protected device to determine the concentration of a specified chemical species.

There is additionally provided a lipid membrane-based gas sensor. The sensor includes a gas-permeable, hydrated upper layer attached to an underlying lipid membrane. Furthermore, the invention includes a process for using the gas sensor to determine the concentration of an inorganic ion formed from an inorganic ion-forming gas.

26 Claims, 2 Drawing Sheets

LIPID MEMBRANE-BASED DEVICE

This application is related to U.S. Pat. Nos. 4,661,235 and 4,637,861, both to Krull and Thompson.

TECHNICAL FIELD

The present invention relates to a lipid membrane-based device. More specifically, this invention pertains to a protected, lipid membrane-based device, to a lipid membrane-based gas sensor, and to the use of these devices as chemoreceptive transducers for the analysis of specific chemical test species.

BACKGROUND ART

An ordered lipid membrane useful as a chemoreceptive transducer in an electrochemical cell is known, as illustrated by U.S. Pat. Nos. 4,661,235 and 4,637,861, both to Krull and Thompson. Such membranes are modified to include a complexing agent for selectively interacting with a particular analyte of interest. However, a drawback is that these membranes may also interact non-selectively by adsorption/absorption of various species, with resultant undesirable transmembrane current perturbation. Furthermore, exposure of a membrane surface to a sample solution permits membrane damage and unwanted solution convection effects.

Krull et al, Abstract 11-2, 67th Annual CIC Conference (June 1984) disclose advances in Langmuir-Blodgett thin-film deposition technology for providing substrate-stabilized, lipid membrane structures. This abstract mentions techniques for such deposition, including schemes involving gel protection.

Heckmann et al, *Thin Solid Films*, 99: 265 (1983) describe a hyperfiltration membrane. It is an object of this work to produce an active layer on top of a membrane for ion permeability control, thereby providing a decreased electrolyte retention capacity with resultant increased water permeability, compared to conventional membranes. The hyperfiltration membrane is a cross-linked monolayer, prepared by cross-linking surfactants having glucose hydrophilic head groups with epichlorohydrin. To extend the selective permeability of the membrane into the range of molecules of medium size, the incorporation of hydrophobic ionophores and pore molecules into the membrane is proposed.

As illustrated by Thompson et al, *Talanta*, 30: 919 (1983), a gas sensor cell that includes a Teflon TM semipermeable membrane and a bilayer lipid membrane, modified to be selective for ammonium ion, is known. FIG. 5 of this publication depicts calculated values for a hypothetical cell formed by removal of the Teflon membrane, and replacement of the aqueous phase with a hydrated gel-like layer.

To prevent membrane damage and undesirable solution convection effects, there is a need for a protected, lipid membrane-based device useful as a chemoreceptive transducer. The discovery of such a device would constitute an even greater contribution to the art if it could also be used to enhance selectivity by preventing interfering chemical species from reaching the lipid membrane surface. Also needed is an improved lipid membrane-based gas sensor. Such devices would beneficially make possible improved processes for analysis.

DISCLOSURE OF THE INVENTION

It is accordingly an object of the present invention to provide a protected, lipid membrane-based device useful as a chemoreceptive transducer.

It is a further object of the present invention to provide a device of this type that could be used to enhance selectivity by controlling the size of the chemical species that reaches the lipid membrane surface.

It is an even further object to provide an improved lipid membrane-based gas sensor.

It is an additional object to provide improved processes for quantitative and qualitative analysis.

Additional objects, advantages and novel features of the present invention are set forth in the description that follows, and in part will become apparent to those skilled in the art upon examination of the following description or may be learned by practice of the invention.

To achieve the foregoing objects and in accordance with the purpose of the present invention, as embodied and broadly described herein, there is provided a protected, lipid membrane-based device useful as a chemoreceptive transducer for determining the concentration of a specified chemical species. The device includes a porous, ion-permeable, hydratable, membrane-protective layer, and an underlying lipid membrane, which controls ion permeability.

The pores of the membrane-protective layer permit passage therethrough of the specified chemical species, but block passage of a larger material from which the lipid membrane is desirably shielded. The lipid membrane is modified by the incorporation of a complexing agent for selectively interacting with the specified chemical species to increase membrane ion permeability.

In accordance with the present invention, there is also provided a process for using the protected device to determine the concentration of the chemical species in an aqueous electrolytic solution. The process includes forming an electrochemical cell from the device and the aqueous solution. There is then applied across the modified lipid membrane of the device an electrical potential difference. The interaction of the chemical species with the membrane-incorporated complexing agent can then produce an analytical signal based upon an increase in membrane ion permeability. The analytical signal is measured, and the concentration of the chemical species is determined from the measured signal.

Also in accordance with this invention, there is provided a lipid membrane-based gas sensor. The sensor includes a gas-permeable, hydrated, upper layer permeable to an inorganic ion-forming gas, which is attached to an underlying lipid membrane. The lipid membrane includes a complexing agent for selectively interacting with a specified inorganic ion formed by the dissolution of the inorganic ion-forming gas in the hydrated, upper layer, to increase permeability of the lipid membrane to the inorganic ion.

Additionally in accordance with this invention, there is provided a process for using the gas sensor to determine the concentration of the inorganic ion in an aqueous electrolyte solution. The process includes applying an electrical potential difference across the lipid membrane of the gas sensor. As a result, the inorganic ion interacts with the lipid membrane-incorporated complexing agent, to increase the permeability of the lipid membrane to the inorganic ion, thereby producing an analytical signal based upon the increased membrane ion permeability. The analytical signal is measured, and the inorganic ion concentration is determined from the measured signal.

BRIEF DESCRIPTION OF THE DRAWING

Reference is made to the accompanying drawing which forms a part of the specification of the present invention.

BEST MODE PRESENTLY CONTEMPLATED FOR CARRYING OUT THE INVENTION

Figure 1:
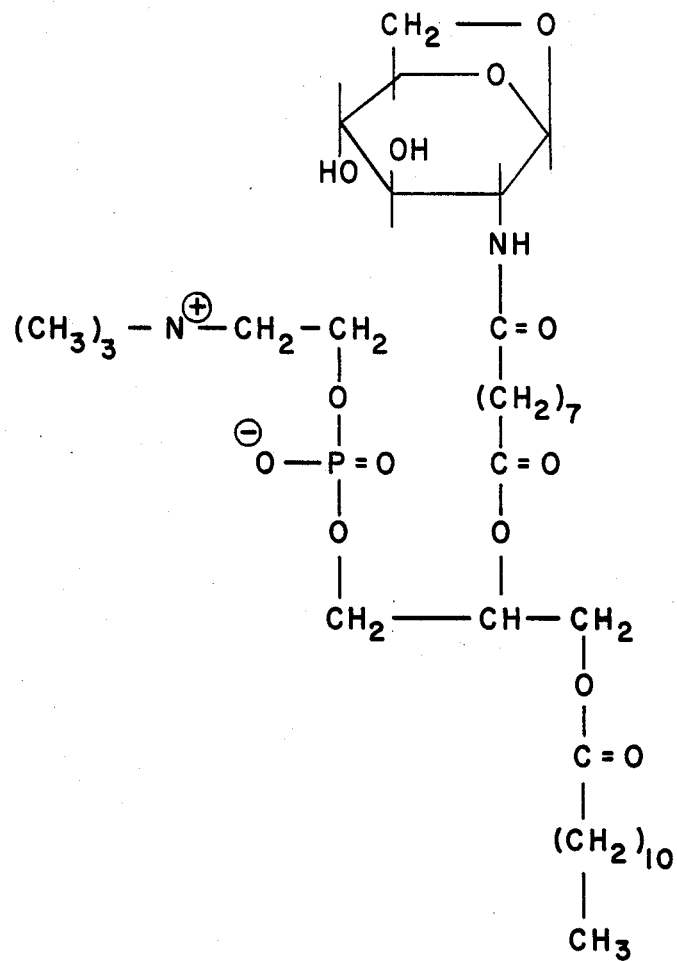
FIG. 1 depicts an exemplary crosslinker useful in forming a lipid membrane-based device in accordance with the present invention.

As explained earlier, the present invention is directed to a novel, protected lipid membrane-based device useful as a chemoreceptive transducer, and to a novel lipid membrane-based gas-sensor. Additionally, this invention is directed to a process for using the protected device for determining the concentration of a specified chemical species in an aqueous electrolytic solution, and to a process for using the gas sensor for determining the concentration of a specified inorganic ion-forming gas.

Lipid membrane-based devices in accordance with the present invention include an upper layer and, attached to the upper layer, an underlying, perturbable lipid membrane. The lipid membrane controls ion permeability, and may be a bilayer or monolayer.

Lipids forming the membrane may be natural or synthetic. Suitable lipids include, but are not limited to, phospholipids such as phosphatidic acid, phosphatidyl glycerol, phosphatidyl choline, phosphatidyl ethanolamine, phosphatidyl serine and phosphatidyl inositol; and sphingolipids such as sphingomyelins. Phosphatidyl serine may be advantageously used as a lipid if biocompatibility is a consideration. The membrane could be formed by a mixture of lipids.

The membrane-forming lipids typically include two long hydrophobic chains. Any long chain useful in forming a natural or synthetic bilayer or monolayer membrane is suitable. Generally, a chain will have a length of from at least six carbon atoms up to and including about thirty, preferably ten to twenty, carbon atoms. Illustrative long hydrophobic acyl chains are caproyl, lauroyl, myristoyl, palmitoyl and stearoyl chains.

The lipid membrane is modified by the incorporation of a complexing agent selective for a specified chemical species (stimulant). Interaction between the complexing agent and the stimulant perturbs the ordered lipid membrane. As a result, an analytical signal based upon an increase in membrane ion permeability is produced.

An essential feature of lipid membrane-based devices according to the present invention is that an upper layer is attached to the lipid membrane. Attachment is preferably by physical bonding.

A suitable method of forming these devices is by the use of a crosslinker that includes moieties that can form the upper layer and bond to the lipid membrane. Thus, a very useful type of crosslinker includes a polymerizable moiety that, upon polymerization, forms the upper layer, and a binding site-providing moiety that is capable of bonding to the lipid membrane.

Useful crosslinkers of this type include polymerizable sugar monomers such as 1,6-anhydro sugars, and long hydrophobic chains for physically bonding to the hydrophobic membrane region. Sugar monomer polymerization beneficially yields a polysaccharide mucous layer as the upper layer. For purposes of this invention, by the term "mucous" is meant a physical structure of polymeric chains which are randomly interwoven to form a mat.

Generally, a suitable long hydrophobic chain will have a length of from at least six carbon atoms up to and including about thirty, preferably ten to twenty carbon atoms. Exemplary long hydrophobic acyl chains are the aforementioned caproyl, lauroyl, myristoyl, palmitoyl and stearoyl chains.

This type of crosslinker advantageously further includes a glycerophosphate moiety, to stabilize the sugar moiety. For example, the lipid system may contain a phosphatidyl moiety as well as acyl chains. One of the acyl chains may carry a 1,6-anhydro sugar group as a terminal group. Interaction of the phosphatidyl moiety with this terminal group of the underlying lipid membrane is then primarily responsible for the physical bonding of the glycophospholipid to the membrane.

An illustrative crosslinker is 2-capramido-1,6-anhydro-2-deoxy-$\beta$-D-glucopyranose. Other crosslinkers can be prepared by reacting 2-amino-1,6-anhydro-2-deoxy-$\beta$-D-glucopyranose with a carboxylic acid having the desired hydrophobic chain length. Thus, myristic acid can be selected for reaction when a fourteen carbon acyl chain is desired.

A commercially available starting material for making 2-amino-1,6-anhydro-2-deoxy-$\beta$-D-glucopyranose, is levoglucosan. Conversion of the 2-hydroxyl group of levoglucosan to a 2-amino group may be achieved by tosylating the 2-hydroxyl and 4-hydroxyl groups, forming an epoxide from the 3-hydroxyl and tosylated 4-hydroxyl groups, opening the epoxide with benzyl alcohol to protect the 4-hydroxyl group with a benzyl moiety, forming an epoxide from the 3-hydroxyl group and the tosylated 2-hydroxyl group, opening the epoxide with ammonia, and restoring the 4-hydroxyl group. An alternative method for making this 2-amino-1,6-anhydro-2-deoxy glucose starts with an N-protected 2-amino-2-deoxy glucose, which is commercially available, and building up the 1,6-anhydro system. Tosylation of the $C_6$-primary hydroxyl, followed by acetylation of the remaining three hydroxyls (on $C_1$, $C_3$ and $C_4$) yields the N-protected 6-tosyl-1,3,4-triacetoxy glucose which, on treatment with base, gives the desired 2-amino-1,6-anhydro-2-deoxy glucose after removal of the protecting group.

Another exemplary crosslinker is the glycophospholipid shown in FIG. 1. This crosslinker is a derivatized phosphatidyl choline containing a 1,6-anhydro-$\beta$-D-glucopyranose as the polymerizable sugar monomer, and a lauroyl moiety as the long hydrophobic chain. Preparation of the glycophospholipid shown in FIG. 1 involves treating 2-amino-1,6-anhydro-2-deoxy glucose with nonanedioic acid to introduce the $C_9$-chain with a terminal carboxyl moiety, which on reaction with lyso-lauroyl lecithin yields the product shown in FIG. 1. Various modifications thereof can be obtained by substituting other straight chain dicarboxylic acids for the nonanedioic acid in the above procedure.

In a further type of crosslinker, the lipid membrane-bonding moiety provides for covalent bonding to the lipid matrix. A covalent-bonding crosslinker could, for instance, be identical to a long hydrophobic chain-containing crosslinker, except that the long chain terminates in a hydroxyl-reactive groups such as a carboxyl group. This modification permits covalent bond formation between the crosslinker long chain and a glycerol hydroxyl group. For example, phosphatidyl glycerol can be tritylated to protect the $C_3$-primary hydroxyl group, then treated with N-($\omega$-carboxy alkanoyl)-1,6-anhydro glucosamine to introduce the sugar moiety onto the $C_2$-position of the lipid, followed by detritylation and treatment with alkanedioic acid.

The length of a crosslinker hydrophobic chain should be selected based upon the lipid membrane hydrophobic chain length. Desirably, a crosslinker chain length should not exceed the membrane chain length and should therefore occupy one chain volume or less.

In forming lipid membrane-based devices according to the present invention using a crosslinker, a low ratio of crosslinker to the membrane-forming lipids is generally employed. By a low ratio is meant a range of typically from about 1:5 to about 1:100, advantageously about 1:10, parts of the crosslinker to the membrane-forming lipids. When each crosslinker has only one chain available for associating into the lipid membrane, this density will provide an association of crosslinker chains into the membrane ranging from about 1 chain per 10 lipids to 1 chain per 1000 lipids. This density provides sufficient association to enable the upper layer to be securely attached to the lipid membrane. An association of about 1 chain per 20 lipids is especially suitable.

On the high density end of the range (1 chain per 10 lipids), fluidity and packing parameters would be greatly affected, and the lipids forming the membrane, would have relatively less mobility. As a result, membrane ion permeability would be relatively less, and the degree of perturbability that a stimulated complexing agent could induce in a lipid matrix would be reduced. Membrane structural stability would be relatively greater on this end of the range.

On the other hand, on the low density end of the range (1 chain per 1000 lipids), the upper layer would be only loosely bound to the lipid membrane, and would therefore be more easily physically displaced. Also, the structural stability of the membrane would be relatively less.

Another useful type of physical bonding requires a very high energy for detaching the upper layer from the lipid membrane. Electrostatic complexation and chemisorption exemplify this type of bonding.

To form the upper layer from polymerizable sugar monomers, UV irradiation may be advantageously employed. A wavelength of abut 254 nm is suitable. The result, with crosslinkers having long hydrophobic chains which have associated with the lipid membrane, is an upper layer that includes long hydrophobic chains embedded in the lipid membrane by a hydrophobic effect.

Figure 2:
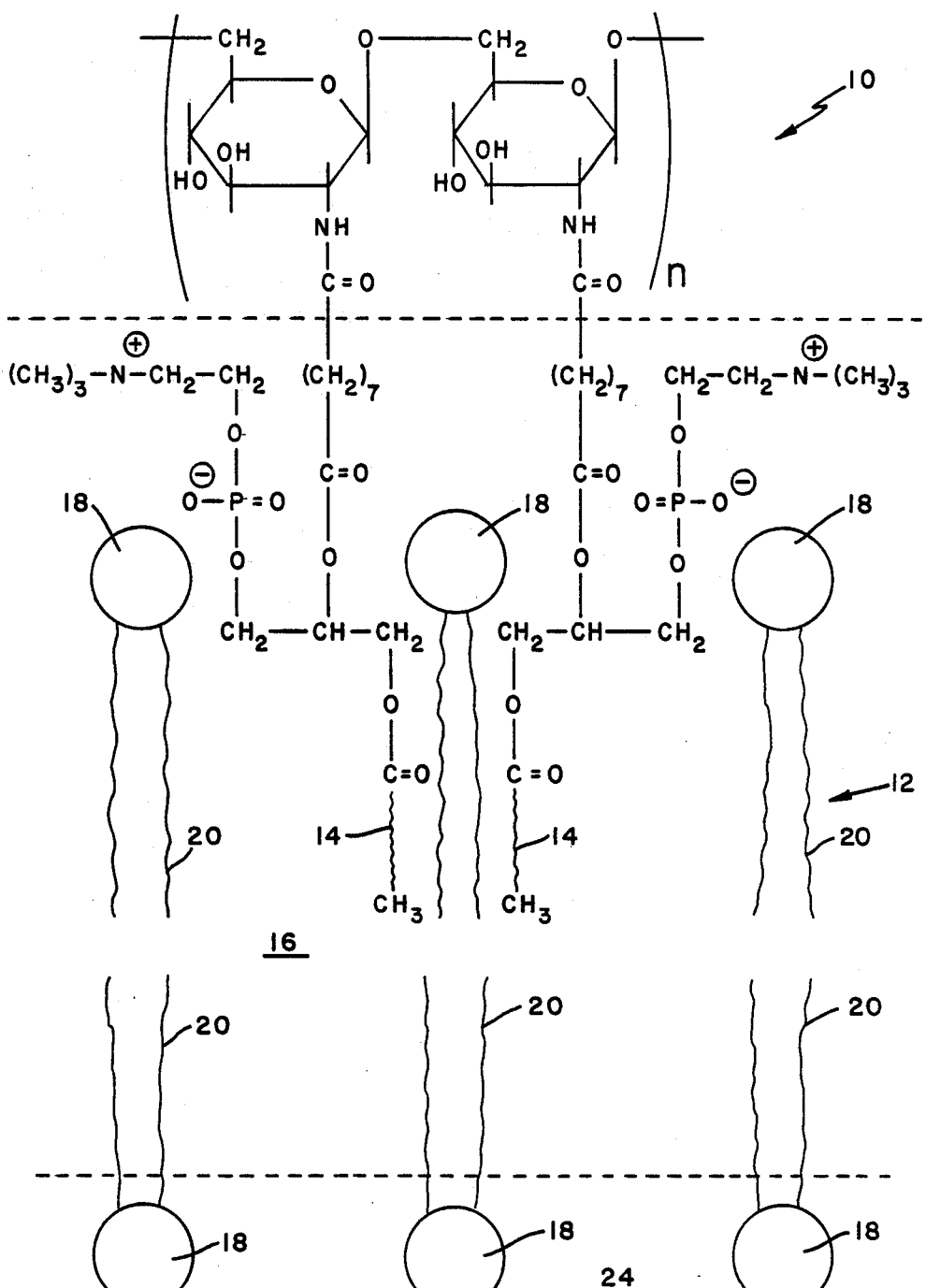
FIG. 2 is a diagrammatic representation of a lipid membrane-based device in accordance with the present invention.

FIG. 2 diagrammatically depicts a mucous layer 10 derived from a glycophospholipid attached by hydrophbic bonding to an ordered, bilayer lipid membrane 12. The mucous layer long chains 14 are shown incorporated into a hydrophobic region 16 of membrane 12. Membrane 12 comprises lipids having polar, hydrophilic head groups 18 and hydrophobic tails 20. The head groups form separate aqueous phase regions 22, 24, which are bordered for illustrative purpose by dotted lines.

If desired, polymerizable sugar monomers lacking lipid membrane-bonding groups (interlinkers), may be added prior to polymerization. During upper layer formation, the interlinkers react with one another to form long polymeric chains, interlinking the upper layer-forming moieties, and building the upper layer thickness. Monomeric interlinkers are suitably used in a ratio ranging from about 1:5 to about 1:100 parts of the upper layer-forming moieties to the monomeric interlinkers. An illustrative interlinker is 2-acetamido-1,6-anhydro-2-deoxy-$\beta$-D-glucopyranose.

Typically, irradiation with UV light (about 254 nm wavelength), for about 5 to 30 minutes at an intensity of about 10 to 100 milliwatts/$cm^2$, may be employed. The length of time and the intensity of irradiation, in conjunction with the concentration of the crosslinker and interlinker, control the degree of density and the thickness of the mucous layer.

Polysaccharides have large dipole moments. Therefore, when the upper layer is a polysaccharide, this characteristic may be used to control membrane dipolar potential. Moreover, the polysaccharide layer can be employed for controlling lipid packing and mobility, and hence the ion energy barrier across the membrane for improvement of the signal-to-noise ratio.

An essential feature of the protected lipid membrane-based device of the present invention is a porous, membrane-protective layer as the upper layer. On the one hand, the pores in the layer are large enough to allow a stimulant to pass through so that it reaches the underlying lipid membrane. However, on the other hand, the average size of the pores is chosen to exclude contaminants or interfering chemical species of larger size than the stimulant from passage through the protective, upper layer.

Of particular concern are organic compounds of a molecular weight of about 1000 or greater. These compounds often threaten membrane destruction, or the possibility of interacting with the complexing agent. Hence, the average pore size is typically chosen to exclude these organic compounds.

As can therefore be understood, the upper layer functions in this device as a barrier layer by screening out the larger-sized chemical species. Furthermore, an additional benefit is provided: selectivity of the complexing agent is enhanced.

A further essential feature of the membrane-protective layer is that it is ion-permeable. Thus, the underlying lipid membrane controls ion permeability of the device. Furthermore, the membrane-protective layer must be hydratable so that ion conduction in the layer is high. Rate-limiting ion conduction must be by the lipid membrane, not by the upper layer.

When the characteristics of porosity, ion-permeability and hydratability are considered, it can be understood that the membrane-protective layer of the protected device is suitably a mucous layer. Advantageously, the membrane-protective layer is a polysaccharide mucous layer. Monomeric sugars for forming a polysaccharide mucous layer are well known in the biochemistry art, and include derivatives of 1,6-anhydro-$\beta$-D-glucopyranose.

As explained earlier, sugar monomers can be polymerized to form a mucous layer by UV irradiation. By, for instance, controlling the time and intensity of the irradiation, the degree of cross-linking and the mucous layer pore size may be regulated. Accordingly, a relatively smaller pore size can be produced by a relatively longer time and/or intensity of irradiation; whereas, a relatively larger pore size results from a relatively shorter time of irradiation.

Control of the pore size also depends upon the density of polymerizable sugar monomer at the layer surface. Thus, a relatively higher monomer density yields a relatively smaller pore size, and a relatively lower monomer density results in a relatively larger pore size.

A complexing agent useful in the protected lipid membrane-based device may be selective for an inorganic ion, or may be a receptor selective for an organic compound.

A useful complexing agent selective for an inorganic ion includes a polypeptide, such as an antibiotic polypeptide. Illustrative antibiotic polypeptides are known in this art and include gramicidin A, valinomycin and nonactin.

The receptor could be, for example, chemically bound in the lipid membrane, and may be a product of nature or a synthetic organic compound. Exemplary receptor-organic compound pairs, all of which are known in this art, are as follows: antibody-antigen, hormone receptor-hormone, enzyme-substrate, enzyme inhibitor-enzyme, and lectin-polysaccharide. An advantageous glycoreceptor is concanavalin A, which is useful for dextran analysis.

An essential feature of a lipid membrane-based gas sensor in accordance with the present invention is a gas-permeable layer as the upper layer. This layer must be hydrated for the gas sensor to function. Therefore, the gas-permeable layer is chosen so that it may be hydrated, and advantageously so that the head groups of the underlying lipid membrane can assist in maintaining water of hydration after removal of the sensor from a bulk aqueous environment.

A mucous layer is easily hydrated since it is quite polar, and can easily form hydrogen bonds with water due to a high density of hydroxyl groups. Furthermore, a mucous structure is porous, thereby enabling water to be retained in the cavities, as in a sponge. Therefore, the gas-permeable layer may suitably be a mucous layer. An advantageous gas-permeable layer is a polysaccharide, mucous layer. Monomeric sugars for forming a polysaccharide, mucous layer are well known in the biochemistry art, and include derivatives of 1,6-anhydro-$\beta$-D-glucopyranose.

The gas sensor may require a replacement of water to offset evaporation and thereby maintain hydration. This may be achieved by a reservoir of water, which would provide replacement of water as needed, by, for instance, capillary action.

In the gas sensor, the lipid membrane-modifying complexing agent is selective for a specified inorganic ion formed by dissolution of a gas, such as ammonia, in an aqueous portion of the hydrated, upper layer. The upper layer is permeable to the ion-forming gas. Interaction between the complexing agent and the inorganic ion increases permeability of the lipid membrane to the inorganic ion, which results in the production of an analytical signal.

Suitable complexing agents useful in the gas sensor include a polypeptide, such as an antibiotic polypeptide. Illustrative antibiotic polypeptides are known in this art, and include gramicidin A, valinomycin and nonactin.

A procedure for making lipid membrane-based devices in accordance with the present invention will now be described.

An ordered, bilayer lipid membrane is produced from the membrane-forming lipids, using a Langmuir-Blodgett thin-film trough. Afterwards, the lipid structure is modified with a selected complexing agent and added to an aqueous solution.

Crosslinkers, including sugar monomers and long hydrophobic chains, are added to the aqueous solution. The crosslinker chains are spontaneously incorporated into the lipid matrix. Spontaneous incorporation may be assisted by stirring, and slight heating above room temperature may be employed. Chain incorporation is permitted to proceed until a significant density of the crosslinker, typically on the order of about 1 chain per 10 to 30 lipids, is physically bonded to the lipid membrane.

At this point, sugar monomer interlinkers may be added to the mixture. Mucous layer formation is then catalyzed using UV irradiation. In the mucous layer formation, the interlinkers react with one another to form long polymeric chains. As interchain polymerization occurs, an upper polymeric layer physically bonded to the lipid membrane through the hydrophobic interaction between the hydrophobic chains and hydrophobic lipid membrane chains, is formed in situ.

Preferably, a device in accordance with the present invention includes a lipid membrane-stabilizing support. The support may be an ion-conductive support or, as described in U.S. Pat. No. 4,637,861, an electrically conductive, solid substrate.

An exemplary ion-conductive support is a hydrogel, for instance, a polyacrylamide hydrogel. An ordered lipid membrane may be deposited onto this type of support by Langmuir-Blodgett thin film deposition.

Alternatively, the support could be an electrically conductive, solid substrate, the surface of which has been modified to provide reactive binding sites. Surface modification to provide binding sites can be accomplished through conventional chemical means, such as oxidation or nitridation. Oxidation and hydration yield hydroxyl binding sites, and nitridation gives nitrogen-containing binding sites.

An ordered lipid membrane may be anchored to binding sites on the support surface through long chains originating in the membrane-forming lipids. Anchoring may be by covalent bonding. One particularly useful technique for covalent bonding involves the reaction of the support surface reactive sites with a bridging species, such as aminopropyltriethoxysilane, followed by reaction of silane terminal amino groups with terminal carboxyl groups of the lipid long chains.

Illustrative electrically conductive, solid substrates include, but are not limited to, a conductive metal such as silver, platinum and gold; electrolytic glassy carbon; and amorphous silver chloride. Each of these exemplary electrically conductive, solid substrates is amenable to surface modification to form reactive binding sites.

After the organized lipid assembly has been stabilized on a support and modified by a complexing agent, the stabilized membrane may then be added to an aqueous solution. Crosslinkers, including sugar monomers and long hydrophobic chains, may then be introduced into the aqueous solution, and after sufficient association of the crosslinker chains into the lipid matrix has occurred, a device in accordance with the present invention may be produced by sugar monomer polymerization.

The devices of the present invention are useful for determining the concentration of a stimulant in an aqueous electrolyte solution. When an ion conductive support is used, ion current may be measured. On the other hand, if an electrically conductive, solid substrate is used as the support, the change in internal capacitance of the lipid membrane may be measured.

To determine the concentration of a stimulant, a lipid membrane-based device in accordance with the present invention is used, in combination with a reference electrode, an electrometer or a capacitance bridge measurement device, a power supply, and an electrolyte. The concentration of the stimulant is determined as follows: Several known concentrations of the stimulant are used to prepare a calibration curve. Then the same electrical parameter, for example, ion current or capacitance, is measured for an unknown concentration of the stimulant, and the concentration is determined by comparison with the calibration curve.

In the Examples that follow and throughout this description and the claims set forth below, all percentages are by weight/weight, and all procedures are carried out at ambient temperature and pressure, unless otherwise specified.

EXAMPLE 1

An ordered, bilayer membrane assembly prepared from egg-derived phosphatidyl choline is physically bonded to a polyacrylamide support by Langmuir-Blodgett thin-film deposition. Afterwards, a 50 Å×50 Å cross-sectional area density of lecitin known as concanavalin A, is adsorbed onto the lipid membrane surface by hydrophilic effects at a density not exceeding more than 50% of the membrane surface.

The lecitin-modified, supported lipid assembly is placed into an aqueous solution. There is then added to the aqueous solution 2-capramido-1,6-anhydro-2-deoxy-$\beta$D-glucopyranose as a crosslinker. Each molecule of this crosslinker has one hydrophobic chain available for associating with the lipid membrane. The amount of crosslinker added provides a density of 1 part of crosslinker to 10 parts of the membrane-forming lipids.

The mixture is gently stirred and heated slightly above ambient temperature to assist spontaneous incorporation of the hydrophobic chains into the lipid matrix. Once a density of 1 chain per 20 lipids is bound into the lipid matrix, 2-acetamido-1,6-anhydro-2-deoxy-$\beta$-D-glucopyranose is added as an interlinker, in a ratio of 10 parts of the interlinker to 1 part of the crosslinker.

The mixture is then irradiated with UV light (254 nm) for 15 minutes at an intensity of 40 milliwatt to effect a ring-opening polymerization of the sugar monomers to form a mucous upper layer. As a result, there is produced a lipid membrane-based device in accordance with the present invention, having a polyacrylamide support, a complexing agent-modified, ordered lipid membrane physically bonded to the polyacrylamide support, and a polysaccharide mucous layer physically bonded to the lipid membrane.

EXAMPLE 2

Following the procedure of Example 1 except that the irradiation step is appropriately modified, a device in accordance with the prsent invention is prepared with an upper layer having a pore size that will permit a compound having a molecular weight of about 800 to pass through, but that blocks passage of an organic compound having a molecular weight of about 1000 or more. Using this device, an Ag/AgCl reference electrode, an electrometer, a DC power supply, and 0.1M KCl at pH 7 as an electrolyte, a liquid electrochemical cell is prepared. The cell is employed using several known concentrations of a dextran having an average molecular weight of about 800, to prepare a calibration curve. Then an aqueous sample containing an unknown concentration of the dextran is introduced into the electrochemical cell, the conductivity change is measured, and the concentration is determined by comparison of the conductivity change with the calibration curve.

EXAMPLE 3

The procedure of Example 1 is followed except that the lipid membrane is doped with nonactin, which is maintained at a solution concentration of $10^{-5}$M. The resulting gas sensor is used with a constant ionic strength buffer (0.1M LiCl) directly in the gas phase to prepare a calibration curve based upon several known concentrations of ammonia gas. Then an unknown concentration of ammonia gas is analyzed using the gas sensor, and the concentration is determined by comparison with the calibration curve.

EXAMPLE 4

An ordered monolayer of the glycophospholipid (FIG. 1) is prepared by the Langmuir-Blodgett thin-film deposition technique on a polyacrylamide or metal-metaloxide surface. The glycophospholipid is prepared by treatment of 2-amino-1,6-anhydro-2-deoxy glucose with nonanedioic acid, followed by reaction of the resultant addition product with lysolauroyl lecithin, as described, supra. The anhydro sugar moiety of the glycophospholipid, which is laid on the surface as a monolayer, is polymerized by treatment with an etherial solution of borontrifluoride-etherate. Alternatively, polymerization can be effected by exposure to U.V. light of suitable wavelength, say 254 nm. This procedure affords an ordered lipid membrane covalently bonded to a polysaccharide umbrella.

If desired, a 2-acrylamido-1,6-anhydro-deoxy glucose can be utilized as a cross-linking agent in the above-described polymerization procedure to obtain the polysacharide.

The lipid membrane obtained by this procedure is then treated with concanavalin A, followed by cross-linking and U.V. irradiation all as described in Example 1, above, to obtain a lipid membrane-based device in accordance with the present invention.

EXAMPLE 5

A silicon wafer containing an oxide layer of about 1000–1200 Å thickness is refluxed in chloroform for 2 to 3 hours to clean the surface from any adhering hydrocarbons and greasy materials. Thereafter, the chloroform is decanted, and the wafer is dried under vacuum. The dried wafer is then silanized by refluxing it for three hours under a nitrogen blanket with a solution of (3-aminopropyl)triethoxy silane in toluene in the presence of a catalytic amount of triethyl amine. The wafer is taken from the liquid, washed several times with chloroform and acetone, and is then dried in vacuum. The thus silanized wafer is treated with glycophospholipid (formula as shown in FIG. 1, except that it carries a —COOH group in place of the terminal —CH$_3$ group at the acyl chain) in a stirred chloroform solution in the presence of catalytic amounts of dimethylaminopyridine and dicyclohexylcarbodiimide under a nitrogen atmosphere at room temperature for 48 hours. The wafer is thereafter recovered from the reaction mixture, washed several times with chloroform, dried under vacuum and stored under nitrogen.

The preparation of the glycophospholipid from phosphatidyl glycerol is as described, supra.

The phosphoglycolipid covalently bound to the silicon surface obtained as described above can be polymerized by exposing the wafer to U.V. light (for example at 254 nm wavelength) or by treatment with borontrifluoride-etherate in anhydrous ether solution. An anhydro-sugar cross-linker may be added during this process, if desired. Further, the procedure described in this Example 5 can be used in sensor applications as described in Examples 2 and 3, above.

The above examples are illustrative of the present invention. It is to be understood that these examples are not in any way to be interpreted as limiting the scope of the invention. Rather, it is intended that the scope of the invention be defined by the claims set forth below. It is contemplated that the invention as hereinafter claimed, will be subject to various modifications, which modifications are within the scope thereof.

INDUSTRIAL APPLICABILITY

The devices of the present invention are useful for the quantitative and qualitative analysis of a specific chemical species, including certain inorganic ion-forming gases such as ammonia.

We claim:

1. A protected, lipid membrane-based device useful as a chemoreceptive transducer for determining the concentration of a specified chemical species, said device comprising:
    a porous, ion-permeable, hydratable, membrane-protective layer, the pores of which permit passage therethrough of said specified chemical species but block passage of a larger material from which an underlying lipid membrane is desirably shielded, and
    attached to said membrane-protective layer, an underlying, lipid membrane which controls ion permeability, said lipid membrane being modified by the incorporation of a complexing agent for selectively interacting with said specified chemical species to increase membrane ion permeability.

2. The device of claim 1, wherein said membrane-protective layer is a mucous layer.

3. The device of claim 2, wherein said mucous layer is a polysaccharide, mucous layer.

4. The device of claim 3, wherein said polysaccharide, mucous layer comprises repeating units derived from 1,6-anhydro-$\beta$-D-glucopyranose.

5. The device of claim 1, wherein attachment between said membrane-protective layer and said lipid membrane, is through a crosslinker that comprises a protective layer-forming moiety and a lipid membrane-bonding group.

6. The device of claim 5, wherein said crosslinker further comprises a glycerophosphate moiety.

7. The device of claim 6, wherein said crosslinker is a glycophospholipid.

8. The device of claim 1, wherein said membrane-protective layer is attached to said lipid membrane by physical bonding.

9. The device of claim 1, wherein said membrane-protective layer is attached to said lipid membrane by hydrophobic bonding.

10. The device of claim 1, further comprising a lipid membrane-stabilizing support.

11. A process for determining the concentration of a selected chemical species in an aqueous electrolytic solution, said process comprising:
    (a) forming an electrochemical cell from said aqueous electrolytic solution and the device of claim 1;
    (b) applying an electrical potential difference across the modified lipid membrane of said device whereby said chemical species interacts with the membrane-incorporated complexing agent to produce an analytical signal based upon an increase in membrane ion permeability;
    (c) measuring said analytical signal; and
    (d) determining said chemical species concentration from the measured analytical signal.

12. The process of claim 11, wherein capacitance or admittance is measured.

13. The process of claim 11, wherein conductivity is measured.

14. A lipid membrane-based, gas sensor comprising a gas-permeable, hydrated, mucous upper layer permeable to an inorganic ion-forming gas, and attached to an underlying lipid membrane, said lipid membrane including a complexing agent for selectively interacting with a specified inorganic ion formed by dissolution of said inorganic ion-forming gas in the hydrated, upper layer, to increase permeability of said lipid membrane to said specified inorganic ion.

15. The gas sensor of claim 14, where said hydrated, mucous upper layer is formed from a polymerizable sugar monomer.

16. The gas sensor of claim 15, wherein said mucous layer is a polysaccharide, mucous layer.

17. The gas sensor of claim 16, wherein said polysaccharide, mucous layer comprises repeating units derived from 1,6-anhydro-$\beta$-D-glucopyranose.

18. The gas sensor of claim 14, wherein attachment between said upper layer and said lipid membrane, is through a crosslinker that comprises an upper layer-forming moiety and a lipid membrane-bonding group.

19. The gas sensor of claim 18, wherein said crosslinker further comprises a glycerophosphate moiety.

20. The gas sensor of claim 19, wherein said crosslinker is a glycophospholipid.

21. The gas sensor of claim 14, wherein said upper layer is attached to said lipid membrane by physical bonding.

22. The gas sensor of claim 21, wherein said upper layer is attached to said lipid membrane by hydrophobic bonding.

23. The gas sensor of claim 14, further comprising a lipid membrane-stabilizing support.

24. A process for determining the concentration of a specified inorganic ion formed by dissolution of an inorganic ion-forming gas in an aqueous electrolytic solution, said process comprising
    (a) applying an electrical potential difference across the lipid membrane of the gas sensor of claim 14, whereby said inorganic ion interacts with the lipid membrane-incorporated, complexing agent to increase the permeability of said lipid membrane to said inorganic ion, thereby producing an analytical signal based upon the increased membrane ion permeability;
    (b) measuring said analytical signal; and
    (c) determining said inorganic ion concentration from the measured analytical signal.

25. The process of claim 24, wherein capacitance or admittance is measured.

26. The process of claim 24, wherein conductivity is measured.

* * * * *